(12) United States Patent
Conte et al.

(10) Patent No.: US 10,436,748 B2
(45) Date of Patent: Oct. 8, 2019

(54) IDENTIFYING ILLICIT DRUGS AND THEIR METABOLITES USING A PORTABLE ELECTROANALYTICAL SYSTEM

(71) Applicant: POCKET LABORATORIES, LLC, Gaithersburg, MD (US)

(72) Inventors: Sean Conte, Gaithersburg, MD (US); Christopher Anthony Cassano, Oakland, CA (US); Michael Albin Grisanti, Owego, NY (US); Corey Letcher, Floral Park, NY (US)

(73) Assignee: POCKET LABORATORIES, LLC, Gaithersburg, MD (US)

( * ) Notice: Subject to any disclaimer, the term of this patent is extended or adjusted under 35 U.S.C. 154(b) by 160 days.

(21) Appl. No.: 15/381,101

(22) Filed: Dec. 15, 2016

(65) Prior Publication Data

US 2017/0168014 A1    Jun. 15, 2017

Related U.S. Application Data

(60) Provisional application No. 62/267,689, filed on Dec. 15, 2015.

(51) Int. Cl.
  *G01N 27/416* (2006.01)
  *G01N 27/48* (2006.01)
  (Continued)

(52) U.S. Cl.
  CPC ......... *G01N 27/48* (2013.01); *G01N 27/416* (2013.01); *G01N 33/227* (2013.01); *G01N 33/48707* (2013.01); *G01N 33/94* (2013.01)

(58) Field of Classification Search
  CPC ...... G01N 27/26; G01N 27/27; G01N 27/416; G01N 27/48; G01N 33/0009;
  (Continued)

(56) References Cited

U.S. PATENT DOCUMENTS

2007/0276611 A1* 11/2007 Lorimer ............... G01N 27/48
                                                          702/25
2008/0045825 A1*  2/2008 Melker .................. A61B 5/083
                                                          600/365
(Continued)

OTHER PUBLICATIONS

Barón-Jaimez et al. "Anodic stripping voltammetry—ASV for determination of heavy metals", Journal of Physics: Conference Series 466 (2013) 012023 (Year: 2013).*

(Continued)

*Primary Examiner* — Alexander S Noguerola
(74) *Attorney, Agent, or Firm* — Eversheds Sutherland (US) LLP

(57) ABSTRACT

This disclosure describes methods, apparatuses, and systems to determine the presence of a chemical substance in an environment, by detecting one or more chemical substances in the environment by using at least one sensor that performs one or more electrochemical tests on one or more chemical samples in the environment, and generates one or more electrical signals corresponding to the chemical samples in the environment. The methods, apparatuses, and systems may also receive and process the one or more electrical signals corresponding to the one or more samples from the environment, wherein the methods, apparatuses, and systems compare the electrical signals to electrical signals corresponding to profiles of known chemical substances in the environment to determine if a match exists. The methods, apparatuses, and systems may compare the electrical signals to baseline threshold values of known chemical substances in the environment to determine if there is an excess or lack of the chemical substance. The methods, apparatuses, and systems may compare the electrical signals to both the stored profiles and baseline threshold values of known chemical substances in the environment to determine if known chemical substances are present in the environ- (Continued)

ment. The methods, apparatuses, and systems may display an alert to confirm, deny, or require further testing to confirm or deny the presence of known chemical substances.

19 Claims, 9 Drawing Sheets

(51) Int. Cl.
*G01N 33/487* (2006.01)
*G01N 33/22* (2006.01)
*G01N 33/94* (2006.01)

(58) Field of Classification Search
CPC .......... G01N 33/0022; G01N 33/0057; G01N 33/22; G01N 33/227; G01N 33/94; G01N 33/946; G01N 33/948
See application file for complete search history.

(56) References Cited

U.S. PATENT DOCUMENTS

| | | | | |
|---|---|---|---|---|
| 2011/0140885 | A1* | 6/2011 | Hummer | G08B 21/12 340/539.13 |
| 2012/0315705 | A1* | 12/2012 | Allyn | G01N 33/0075 436/159 |

OTHER PUBLICATIONS

DEA image of a methamphetamine pill, downloaded Sep. 13, 2018, from https://www.dea.gov/galleries/drug-images/narcotics (Year: 2018).*

Methamphetamine entry in at the INCHEM website (IPCS International Programme on Chemical Safety), downloaded Sep. 13, 2018, from http://www.inchem.org/documents/pims/pharm/pim334.htm (Year: 2018).*

Lonsdale et al., "Onsite Measurement of Lead in Gunshot Residues Using Linear Sweep Voltammetry," Modern Environmental Science and Engineering Oct. 2015, vol. 1, No. 4, pp. 192-195 (Year: 2015).*

Product description of the Modern Water PDV6000plus voltammetric instrument downloaded Sep. 13, 2018 from http://na.toocle.com/sell/detail--9293.html (Year: 2018).*

Nermiroski et al., "Universal mobile electrochemical detector designed for use in resource-limited applications," PNAS Aug. 19, 2014, vol. 111, No. 33, pp. 11984-11989 (Year: 2014).*

Kim et al., "Development of a Portable Biosensor System for Pesticide Detection on a Metal Chip Surface Integrated with Wireless Communication," Food Sci. Biotechnol. 24(2), 743-750 (2015) (Year: 2015).*

Abdulameer et al., "Spectroscopic study of (E)-2-(2-hydroxybenzylidenamino) Phenol Crystal and Study of Nonlinear Optical Properties of It," Academic Research International vol. 5(5) Sep. 2014, pp. 65-72 (Year: 2014).*

Muralidharan et al., "Single Crystal Structure and Characterization of 2-Amino-4-methylpyridinium-4-nitrophenolate-4-nitrophenol," Asian Journal of Chemistry; vol. 25, No. 18(2013), 10107-10112 (Year: 2013).*

Palys et al., "The Separation of Overlapping Peaks in Cyclic Voltammetry by Means of Semi-Differential Transformation," Talanta, vol. 38, No. 7, pp. 723-733, 1991 (Year: 1991).*

Jakubowska et al., "Signal Processing in Electrochemistry," Electroanalysis 2011, 23, No. , 553-572 (Year: 2011).*

Agilent manual on OpenLAB and Agilent EZChrom Elite PDA Analysis, edition May, 2007 Document Revision 3.3B/3.2 (Year: 2007).*

ChromQuest 5.0 Chromatography Data System Reference Guide, ThermoScientific CHROM-97253 Revision A Mar. 2008 (Year: 2008).*

* cited by examiner

IDENTIFYING ILLICIT DRUGS AND THEIR METABOLITES USING A PORTABLE ELECTROANALYTICAL SYSTEM

CROSS-REFERENCE TO RELATED APPLICATIONS

This application is related to and claims priority to U.S. Provisional Patent Application No. 62/267,689, filed Dec. 15, 2015. The content of each of the above-referenced applications is hereby incorporated herein by reference in its entirety.

TECHNICAL FIELD

This disclosure generally relates to methods and systems for identifying gunshot residue using a portable electroanalytical system for mobile communication devices.

BACKGROUND

The development of new analytical instruments and methods to perform simple and rapid real-time chemical analysis in the field is becoming increasingly important, especially in resource-limited settings. A potentiostat is an electronic hardware found in many laboratories widely used to identify, quantify, and characterize electroactive species using electrochemistry as a foundation. This instrument is ideal as a general chemical sensor because it is capable of performing diverse electroanalytical experiments when combined with one or more different electrodes. The one or more electrodes may provide selectivity and sensitivity, thus creating boundless electrochemical applications. The current technology for portable potentiostats is focused on standalone or miniaturized devices which rely on computers for functionality. These devices are applicable in many different fields ranging from forensic/security to environmental analysis.

While electrochemical sensors are growing in magnitude and scope, there is a need in the industry for greater portability, a more refined user interface, and more advanced real-time data analysis incorporated into one system. Some portable devices available now are designed to be standalone; these lack a refined user interface combined with a sophisticated, yet timely, data analysis. Standalone devices are also more difficult to upgrade, which is important for incorporating new testing procedures and data analytics as the science progresses. Devices that require computer tethering for computation do not provide true portability as the user still needs to bring a computer to the testing location. Additionally, most computer interface systems are not intuitive and require some software training prior to use. Devices tethered to computers have the added benefit of software upgradability, but as mentioned previously, the portability factor decreases. With the shortcomings currently present in the field, this invention seeks to provide better portability, an intuitive user-interface, quick and efficient software upgrades, and real-time data processing all in a single system.

DETAILED DESCRIPTION

Figure 1:
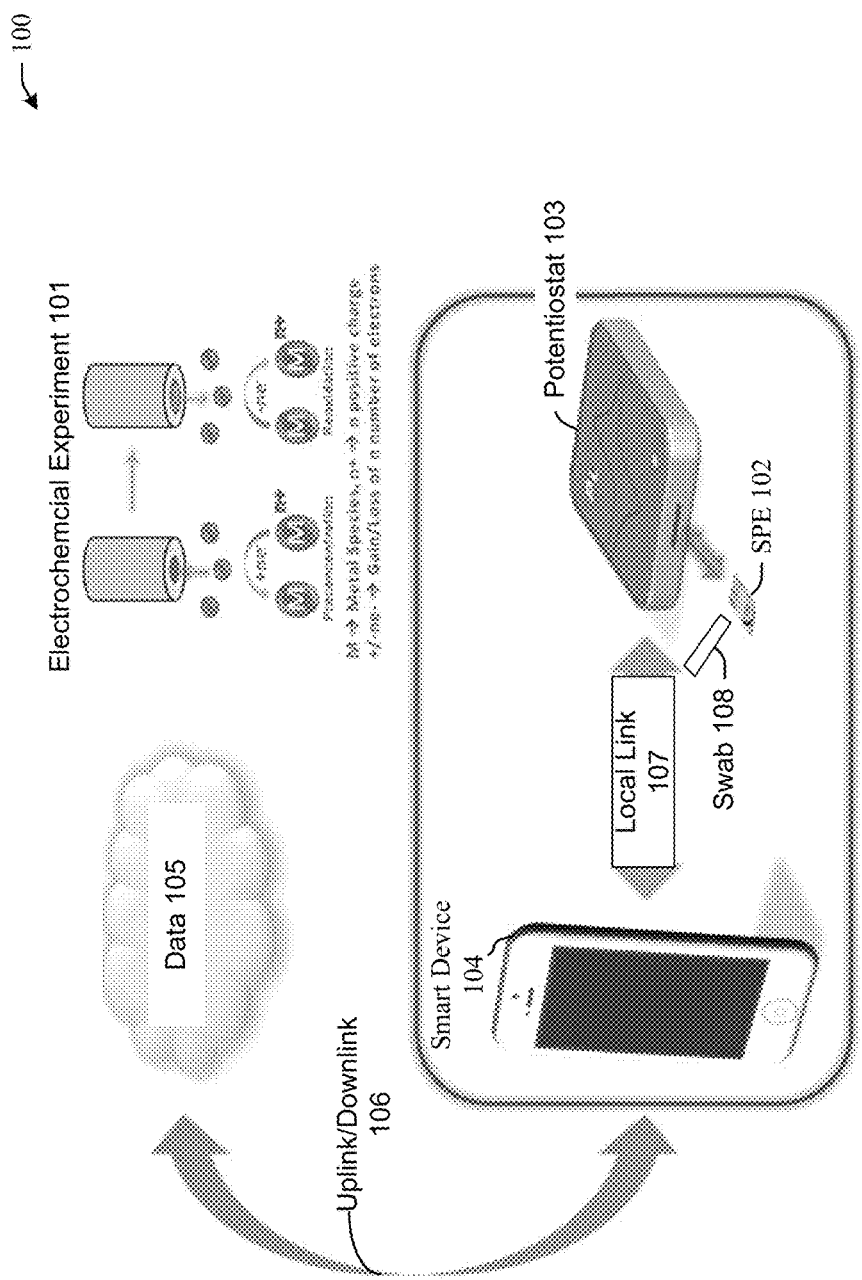
FIG. 1 depicts a network diagram illustrating an example network environment of an illustrative portable electroanalytical system and mobile communication device, in accordance with one or more example embodiments of the disclosure.

Example embodiments described herein provide certain systems, methods, and devices, for identifying gunshot residue using a portable electroanalytical system for mobile communication devices. In some embodiments the portable electroanalytical system may be communicatively coupled to a desktop computer, server, supercomputer, mainframe computer, and/or any other non-transitory computing device. In other embodiments the electroanalytical system may not be portable.

The electrochemical system may be comprised of one or more computing devices (computers or smart devices), a small, portable, battery powered potentiostat, a screen printed electrode (SPE), and a testing substrate. The potentiostat may include bluetooth technology to enable wireless connectivity with the one or more computing devices. It may also be equipped with USB connectivity to allow for compatibility with older systems, to provide an alternate source of power from the one or more computing devices during extended experiments, and to assist with firmware updates should they be needed. The potentiostat may collect data, store it in an internal memory (i.e., Internal Memory 204) and then transfer the data over bluetooth or USB to the one or more computing devices where the data is processed and the results displayed on a user device (i.e., User Device 202). These results are then stored on the computing device, or sent over a network connection to a secondary storage system (e.g. secure server, cloud). The SPE may be a removable part that is thrown away or reused depending on the testing and situation. The testing substrate may be added to the SPE and then the SPE may plug into the potentiostat. In some embodiments the use of non SPE electrodes may be used. If non SPE electrodes are used, an adapter to accommodate this is attached to the potentiostat where the SPE is normally inserted. The type of test and the potentiostat experiment settings may be entered on a user's smart device and sent to the potentiostat to run the experiment. The potentiostat may then send the experiment data back to the smart device for higher level processing, display and graphing, storage, and transfer via network connection.

This system may be an effective mobile chemical detector for many different applications including but not limited to forensic/security (e.g. narcotics, explosives, gunshot residue), environmental (e.g. heavy metal, pesticide, phenol), and biomedical testing (e.g. glucose, antibody).

Increasing forensic and security concerns have created major demands for effective field-deployable analytical tools for detecting explosives, narcotics, and gunshot residue (GSR) in a reliable, swift, and simple manner. In the case of gunshot residue, efficient field testing kits are lacking compared to narcotics and explosives. The two major presumptive colorimetric GSR kits that exist are diphenylamine (DPA) and sodium rhodizonate (SR) based analysis. DPA detects nitrates, while SR tests for lead and barium. The DPA test suffers from very high false positive rate because nitrates can be found in common sources such as fertilizer, cigarette smoke, food additives, and even in cosmetic products. Because nitrates are found in some of the environments where tests may be performed, the DPA test may detect nitrates that are a part of the environment, that have not been deposited by the residue of a gunshot. The color change observed for SR analysis is sometimes too subtle (based on small particles or low concentration) which causes inaccuracy as well.

Due to the shortcomings of these colorimetric tests, a non-subjective method to detect a small quantity of the inorganic content from the GSR efficiently is needed. The metallic composition of GSR is detected with high sensitivity by applying anodic stripping voltammetry. The objective is to show the detection of lead and other heavy metal elements (e.g. Cu, Sb, etc. . . . ).

The advancement of screen printing technology over the years has enabled economical electrochemical sensors to be produced rather easily and inexpensively making them an attractive option as an analytical probe. Screen printed electrodes (SPEs) provide a major advantage over traditional electrodes due to their unique properties: low-cost, disposability, ready-to-use, simplicity, and portability. For this reason, SPEs are ideal electrochemical probes for field GSR analysis.

Together with SPEs, the potentiostat-smart device system has the potential to become a very powerful investigation tool for law enforcement. The one or more computer-executable instructions stored in Internal Memory 404, which when executed by a processor (not shown) in Digital Microcontroller Circuitry 403 may process the electrochemical signals obtained from anodic stripping voltammetry of GSR and may provide an automated detection result. The one or more computer-executable instructions may also display an evidence form, on User Device 402, with supplementary features such as GPS, sample barcode reader, and cloud data storage to provide a high-level information tracking. The obtained result provides immediate actionable intelligence to law enforcement to assist in the investigation without potentially compromising the confirmatory analysis required to support the legal case.

An electrochemical system disclosed is comprised of a potentiostat coupled with one of multiple types of smart devices, including but not limited to: a computer, smart phone, or a tablet. Furthermore, the potentiostat may use bluetooth technology as a method of data transmission. The potentiostat disclosed herein is fully portable, allowing its usage as a general chemical sensor in many different fields including but not limited to forensic/security, environment, and biomedical applications. One or more computer-executable instructions may be stored in one or more computer-readable media in a mobile device that may be executed by one or more processors in the mobile device to update the computer-executable instructions (i.e., remove certain computer-executable instructions and/or add new computer-executable instructions). Utilizing software applications with the coupled system enables for robust, real-time data analytics, while providing an intuitive, user-friendly interface. The system employs the smart device to upload data to the cloud or to the user's data storage of choice, providing unprecedented level of data storage and traceability.

FIG. 1 depicts a network diagram illustrating an example network environment (i.e., network environment 100) of an illustrative portable electroanalytical system for a mobile communication device, in accordance with one or more example embodiments of the disclosure. Example network environment 100 may comprise, screen printed electrode (SPE 102), Potentiostat 103, Smart Device 104, and Data 105.

An electrochemical experiment (Electrochemical Experiment 101) may be performed and SPE 102 may be used, to collect one or more samples (i.e., samples of residue) from Electrochemical Experiment 101 and may be analyzed by a potentiostat (Potentiostat 103) for one or more metallic materials in the samples of residue using one or more anodic stripping voltammetry techniques. In some embodiments, a swab might be used (e.g., Swab 108).

Potentiostat 103 may generate one or more digital samples corresponding to the analyzed samples of residue. A mobile device (Smart Device 104) may communicate the digital samples from Potentiostat 103 to one or more storage media (i.e., Data 105) using one or more wireless technologies (i.e., Bluetooth, Wi-Fi, 6LowPan, Zigbee, RFID, WiMAX, cellular, or any other communication protocol capable of sending and receiving data wirelessly). Data 105 A first bidirectional link (Uplink/Downlink 106) may be established between Smart Device 104 and Data 105. In some embodiments Smart Device 104 may be a personal hotspot router that routes the digital samples generated at Potentiostat 103 to Data 105. Data 105 may send one or more analytical tests to Potentiostat 103 via Smart Device 104. A second bidirectional communication link (i.e., Local Link 107) may be established between Smart Device 104 and Potentiostat 103, to send the one or more analytical tests to from Smart Device 104 to Potentiostat 103 and the digital samples from Potentiostat 103 to Smart Device 104. Local Communication Link 106 may comprise wired technologies (i.e., USB 1.1, 2.0, 3.0, 3.1, FireWire, HDMI, Ethernet) and/or wireless technologies (i.e., Bluetooth, Wi-Fi, 6LowPan, Zigbee, RFID, WiMAX).

Figure 2:
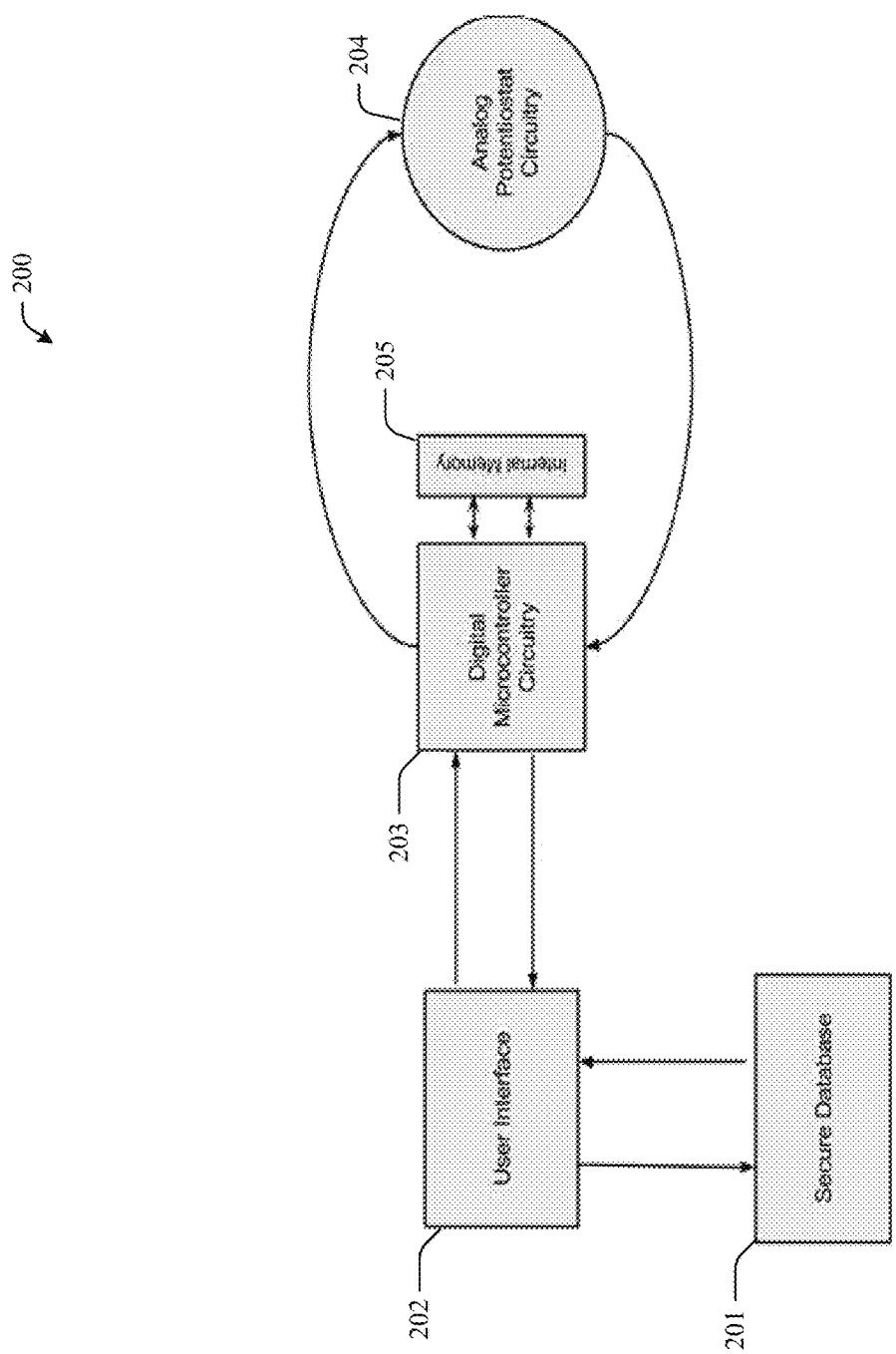
FIG. 2 depicts a diagram illustrating a logical interaction between one or more electrical circuits comprising a portable electroanalytical system and a mobile communication device, in accordance with one or more example embodiments of the present disclosure.

FIG. 2 depicts a diagram illustrating a logical interaction between one or more electrical circuits comprising a portable electroanalytical system and a mobile communication device, in accordance with one or more example embodiments of the present disclosure. Example environment 200 may include one or more computer-readable storage media (Secure Database 201) for storing data (i.e., results of analytical tests), at least one mobile device (User Device 202) for displaying the results of the analytical tests in one or more graphical illustrations, and a potentiostat (i.e., Potentiostat 103) comprising one or more microcontrollers (Digital Microcontroller Circuitry 203) that may be internal to Potentiostat 103, and one or more analog potentiostat circuits (Analog Potentiostat Circuitry 204) and computer-readable memory (Internal Memory 205). Secure Database 201 may be similar to or the same as Data 105 in FIG. 1. A bidirectional communication link may be established between User Device 202 and Secure Database 201 using one or more public and/or private key encryption technologies. Secure Database 201 may send one or more analytical tests to User Device 202, which may be decrypted by User Device 202 using a public key. User Device 202 may encrypt the results of the one or more analytical tests and send the encrypted results to Secure Database 201. User Device 202 may send one or more test parameters, corresponding to the one or more analytical tests, to Digital Microcontroller Circuitry 203 which may in turn send one or more commands to Analog Potentiostat Circuitry 204 which may execute the one or more analytical tests using the one or more test parameters. One or more screen printed electrodes (i.e., SPE 102) may be brought into contact with Analog Potentiostat Circuitry 104, which may in turn generate one or more electrical analog signals that may be sampled using an Analog-to-Digital Converter (ADC) in Digital Microcontroller Circuitry 203 to generate one or more digital samples corresponding to the one or more electrical analog signals. SPE 102 or Swab 108 may be used to swab an area of an environment (e.g., hand, desk, wall, floor, etc.) to collect one or more samples of material that may be tested for using the one or more analytical tests. When SPE 102 is inserted in Analog Potentiostat Circuitry 204, Analog Potentiostat Circuitry 204 generates the one or more electrical analog signals after electrolyte is applied to the SPE 102 either via Swab 108 or via electrolyte droplets. One or more computer-executable instructions may be stored in Internal Memory 205, to cause Digital Microcontroller Circuitry 203 to send the one or more commands to Analog Potentiostat Circuitry 203 to generate the one or more electrical analog signals. Internal Memory 205 may also store one or more computer-readable instructions to cause Digital Microcontroller Circuitry 203 to receive the one or more electrical analog signals and digitize the data using an ADC included therein. Digital Microcontroller Circuitry 203 may send the digitized data (i.e., digitized samples) to User Device 202 to be displayed on a user interface (not shown). The user interface may display a graph, chart, and/or one or more images corresponding to the one or more materials identified by the one or more analytical tests.

Figure 3:
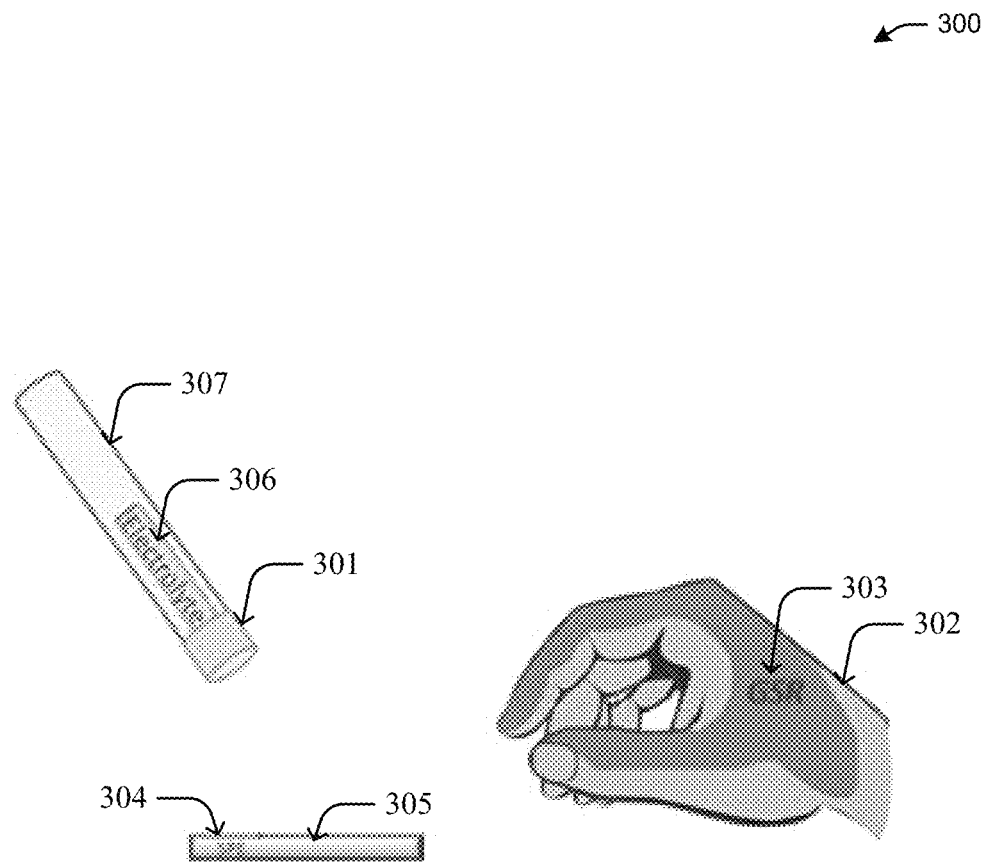
FIG. 3 depicts an illustrative screen printed electrode, swab, and electrolyte solution, in accordance with one or more example embodiments of the present disclosure.

FIG. 3 depicts an illustrative screen printed electrode and electrolyte solution, in accordance with one or more example embodiments of the present disclosure. In order to collect samples of metallic material from an environment, a swab (Swab 301) may be applied to the environment containing gunshot residue (GSR 303). In some embodiments, Swab 301 may be applied to a human body part (User's Hand 302). After Swab 301 is applied to the environment or body part, a user may squeeze the Swab 301 and an electrolyte may be applied to the Swab 301. A user may then apply Swab 301, with the electrolyte and sample, to a SPE (SPE 304). SPE 304 may SPE 304 may be printed onto a wand (Wand 305). Wand SPE 304 may be the same as SPE 201.

Swab 301 may be used collect GSR (or sample of interest) first. An electrolyte must be applied to perform an electrochemical analysis. In some embodiments, the electrolyte may be in the form of a liquid that is housed within an ampoule (Ampoule 306). A user may apply pressure to a stick (Stick 307) housing Ampoule 306 to crack Ampoule 306 so that liquid is applied to Swab 301. In some embodiments, Swab 301 may be wet first before samples are collected. SPE 304 may comprise one or more working, reference, and counter electrodes (not shown). When Swab 301 is applied to SPE 304 it may cover the one or more electrodes, with the working electrode capturing the majority of the area of the sample on Swab 301. The working electrode may be the electrode that measures the chemical process.

In some embodiments, a thin paper may be applied beforehand to the reference and counter electrodes and Swab 301 may be applied directly to the working electrode. Because Swab 301 is wet when applied to the working electrode, the liquid on Swab 301 may also wet the thin paper applied to the reference and counter electrodes. This may in turn wet the reference and counter electrodes thereby allowing the working electrode to measure the chemical process.

Figure 4:
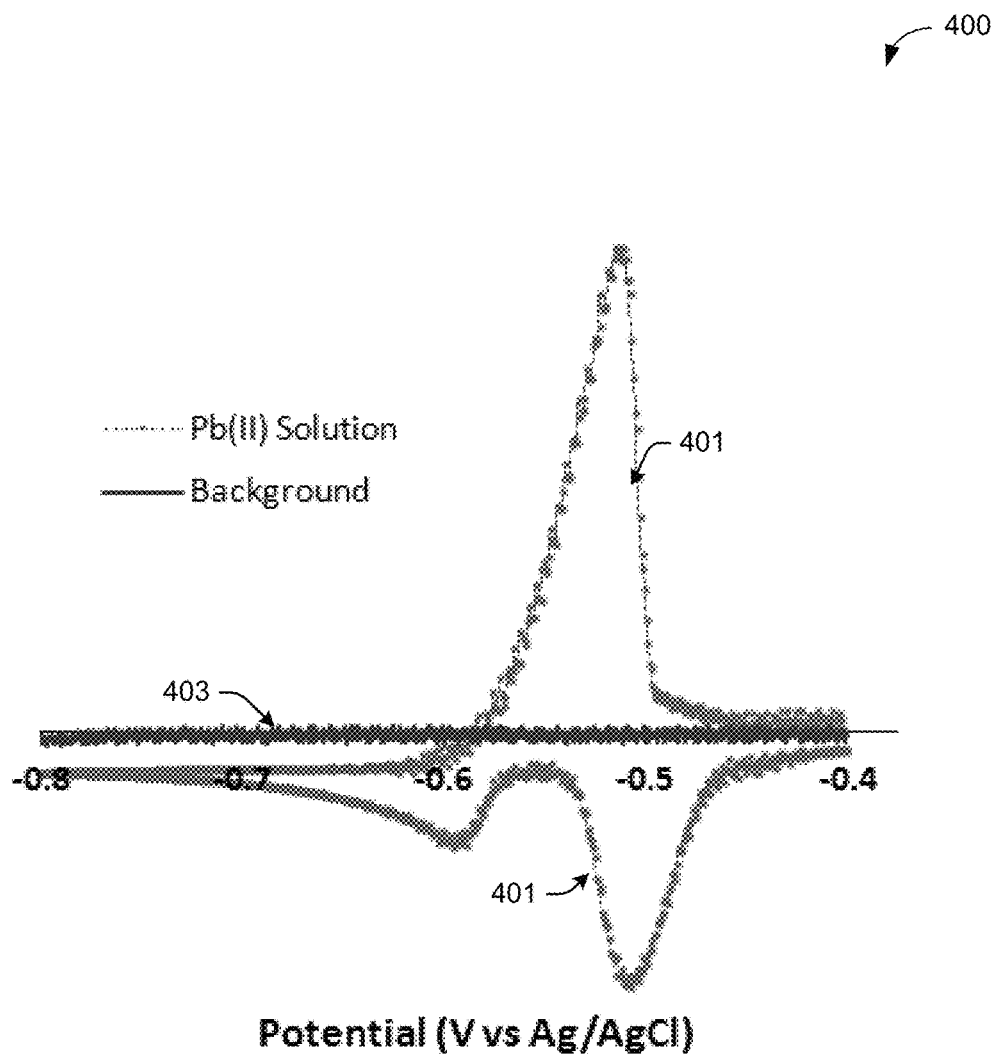
FIG. 4 illustrates a cyclic voltammogram, in accordance with one or more example embodiments of the present disclosure.

FIG. 4 depicts a cyclic voltammetric response of ionic lead using a gold-based electrode. The cyclic voltammetric response may be used to detect one or more metallic substances in a sample from an environment. The objective may be to determine if lead and other heavy metal elements (e.g. Cu, Sb, etc. . . . ) are present in the sample. The presence of multiple heavy metal species native to GSR provides some certainty that a firearm was discharged thereby producing gunshot residue. The probability of multiple heavy metals being present caused by something other than GSR is very low, but the test is still presumptive as it does not perform a particle analysis to prove that the components did indeed come from a fired weapon. However, confirmatory testing (e.g. scanning electron microscopy) on the analyzed sample is possible since electrochemical techniques are non-destructive. The cyclic voltammogram response may correspond to a cyclic voltammogram of 0.5 milligrams per milliliter of lead nitrate solution (Pb(II) Solution 401) and a background (Background 403) using gold based SPE. As mentioned above an electrolyte may be used to test for GSR. In FIG. 4 a 0.2M acetate buffer electrolyte is depicted with a pH of 4.2. A sweep rate of 10 millivolts per second may be used to generate the cyclic voltammetric response.

Figure 5:
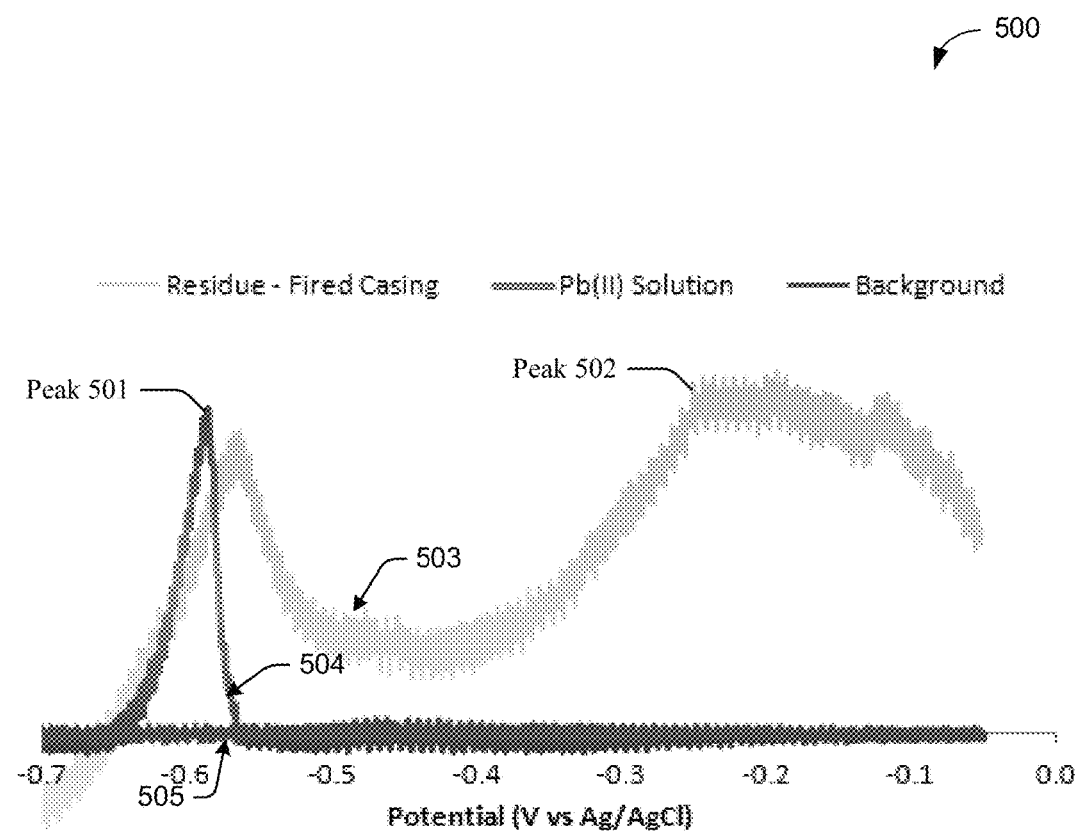
FIG. 5 illustrates a linear sweep anodic stripping analysis, in accordance with one or more example embodiments of the present disclosure.

FIG. 5 illustrates a linear sweep anodic stripping analysis, in accordance with one or more example embodiments of the present disclosure. The linear sweep anodic stripping analysis may correspond to one or more electrochemical signals from anodic stripping voltammetry of ionic lead in a solution, and a one round 9 mm (Fiocchi) gunshot residue collected from a hand after firing a round using a swab applicator stick (Swab 108) applied onto a gold-based SPE (i.e., SPE 201). The residue may contain lead as shown by a narrow peak (Peak 501) around −0.55V. The two peaks (Peak 502) centered at 0.05V may be attributed to antimony/copper. The supporting electrolyte used in the linear sweep anodic stripping analysis may be a 0.2M acetate buffer with pH 4.2. A deposition potential of −0.8 Volts vs Silver/Silver Chloride, with a deposition time of 150 seconds, and sweep rate 10 millivolts per second may be used to generate the linear sweep anodic stripping analysis. GSR—One Round Swab 503 may be an electrochemical response corresponding to residue from a fired round and Pb(II) Solution 504 may be an electrochemical response corresponding to a lead nitrate solution.

Figure 6:
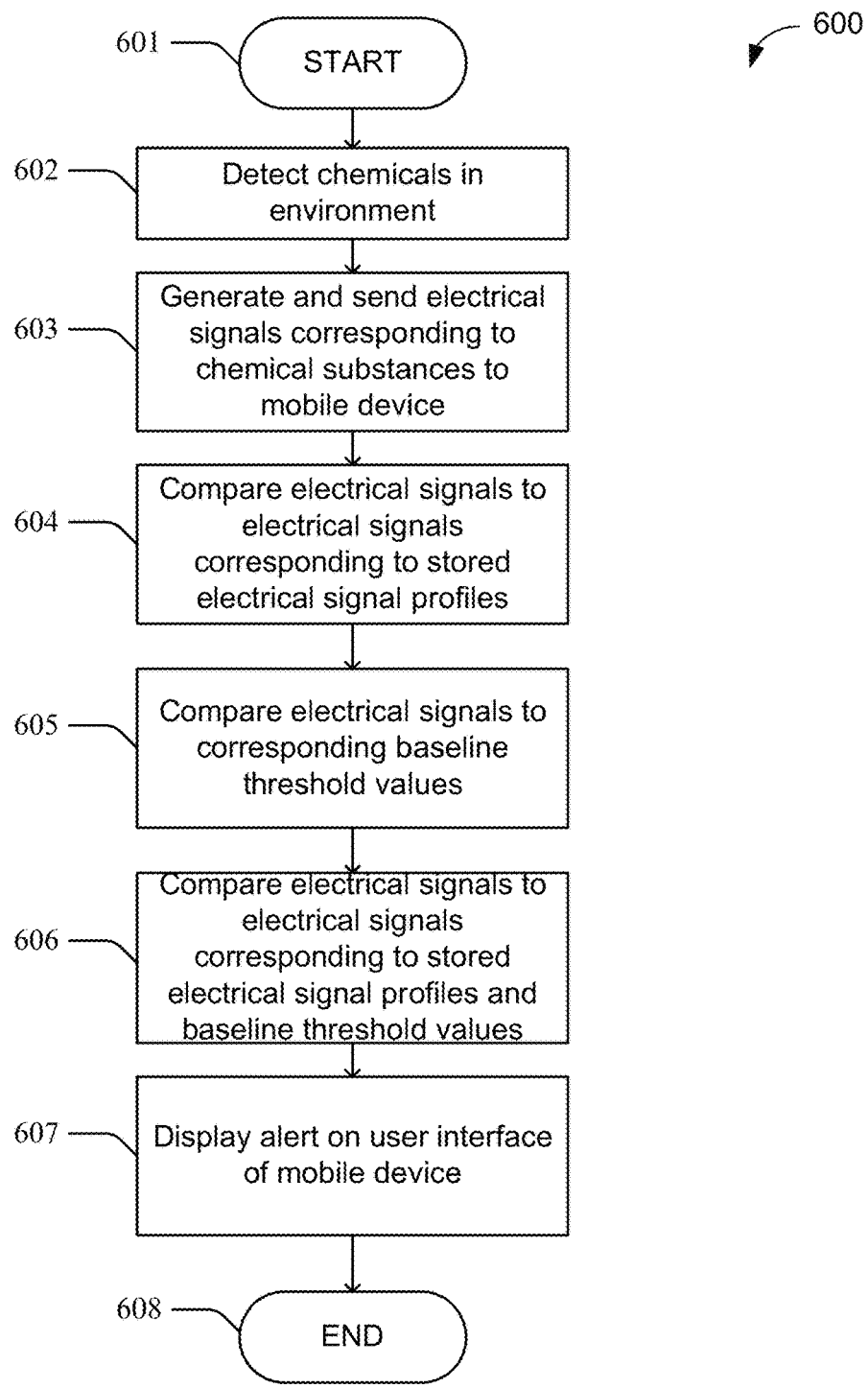
FIG. 6 illustrates a flow diagram of an illustrative process for detecting a chemical substance associated with a gunshot residue, in accordance with one or more example embodiments of the present disclosure.

FIG. 6 illustrates a flow diagram of an illustrative process for detecting a chemical substance associated with a gunshot residue, in accordance with one or more example embodiments of the present disclosure. Process 600 may be executed by one or more first processors in a potentiostat (i.e., Potentiostat 103) and one or more second processors in mobile device (Smart Device 104), in response to executing one or more first instructions stored on one or more first computer-readable media (i.e., Internal Memory 204) in Potentiostat 103 and one or more second instructions stored on one or more second computer-readable media in Smart Device 104.

After initial start step 601, a potentiostat may detect one or more chemical substances in an environment in step 602 by performing one or more electrochemical tests on one or more chemical samples retrieved from the environment. For example, a swab (i.e., Swab 301) may collect one or more samples from an environment containing chemical substances to be tested for using one or more electrochemical tests, and brushed against one or more electrodes on a SPE (i.e., SPE 201) that may then be inserted into the potentiostat. The potentiostat, may generate one or more electrical signals corresponding to the chemical substances in the environment, and send the one or more electrical signals to a mobile device (i.e., User Device 104) in step 603.

In step 604, the mobile device may receive and process the one or more electrical signals from the potentiostat and compare the one or more electrical signals to electrical signals corresponding to stored profiles of chemical substances associated with GSR to determine if a match exists. In step 605, the mobile device may compare the electrical signals corresponding to baseline threshold values of chemical substances associated with GSR to the one or more electrical signals, to determine if there is an excess or lack of the chemical substance. In step 606, the mobile device may compare the electrical signals corresponding to both the stored profiles and baseline threshold values of known chemical substances in the environment to the one or more electrical signals, to determine if there are any chemical substances corresponding to GSR. The mobile device may then display an alert on a user interface on the mobile device to confirm or deny the presence of a chemical substance associated with GSR in step 607. After step 607 the process may end (608).

Figure 7:
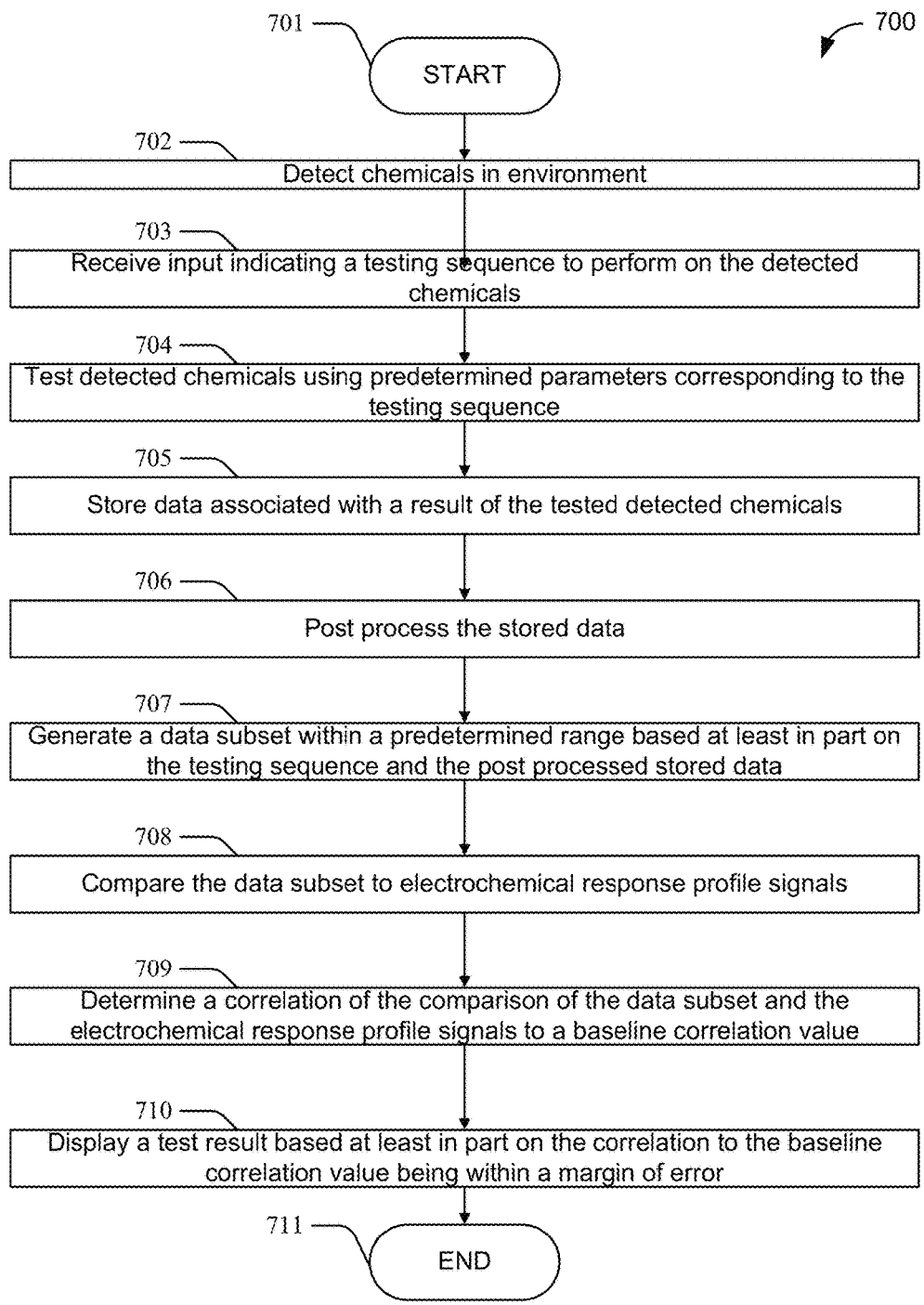
FIG. 7 illustrates a flow diagram of an illustrative process for detecting a chemical substance associated with a gunshot residue, in accordance with one or more example embodiments of the present disclosure.

FIG. 7 is illustrates a flow diagram of an illustrative process for detecting a chemical substance associated with a gunshot residue, in accordance with one or more example embodiments of the present disclosure. After initial start step 701, the method may detect chemicals in the environment at step 702. At step 703, the method may then receive input indicating a testing sequence to perform on the detected chemicals. At step 704, the method may test detected chemicals using predetermined parameters corresponding to the testing sequence. At step 705, the method may store data associated with a result of the tested detected chemicals. At step 706, the method may post process the stored data. For example, the method may filter, sort, reduce noise in the stored data, and/or average the stored data. At step 707, the method may generate a data subset within a predetermined range based at least in part on the testing sequence and the post processed stored data. At step 708, the method may compare the data subset to electrochemical response profile signals. In some embodiments, one or more of the following techniques may be used to compare the data subset to electrochemical response profile signals. For example, in some embodiments, an absolute maximum or minimum technique may be used to compare one or more absolute maximum or minimum points in the data subset to one or more absolute maximum or minimum points corresponding to the electrochemical response profile signals. In other embodiments, a slope comparison technique may be made between a plot of one or more points in the data subset to a plot of one or more points corresponding to the electrochemical response profile signals. Yet in other embodiments, a first order and/or second order derivatives of the plot of one or more points of the data subset may be compared to a first order and/or second order derivative of the plot of one or more points corresponding to the electrochemical response profile signals. This may be referred to as derivative technique. For example, a derivative of GSR—One Round Swab 503 may be determined by taking a difference between two points on GSR—One Round Swab 503 and dividing the result by a difference between a first potential (V) value and a second potential (V). In other embodiments, the area under the plot of one or more points in the data subset may be compared to the area under the plot of one or more points corresponding to the electrochemical response profile signals. This may be referred to as an integral test. This may be referred to as an integration technique. For instance, the area under GSR—One Round Swab 503 may be determined by sampling GSR—One Round Swab 503 n times, wherein n can be any natural number and determining an area under a rectangle connecting adjacent samples of GSR—One Round Swab 503. As an example, n may be equal to 100,000, therefore a difference between adjacent samples may be taken (i.e., different points on GSR—One Round Swab 503) and the resulting difference may be multiplied by the height of a horizontal line going through the adjacent samples. That is a rectangle may be formed using the samples in order to determine a total area under the curve. At step 709, the method may determine a correlation of the comparison of the data subset and the electrochemical response profile signals to a baseline correlation value. If there is more than one data subset, the method may return to step 708. At step 710, the method may display a test result based at least in part on the correlation to the baseline correlation value being within a margin of error. At step 710, the method may end (step 711).

Figure 8:
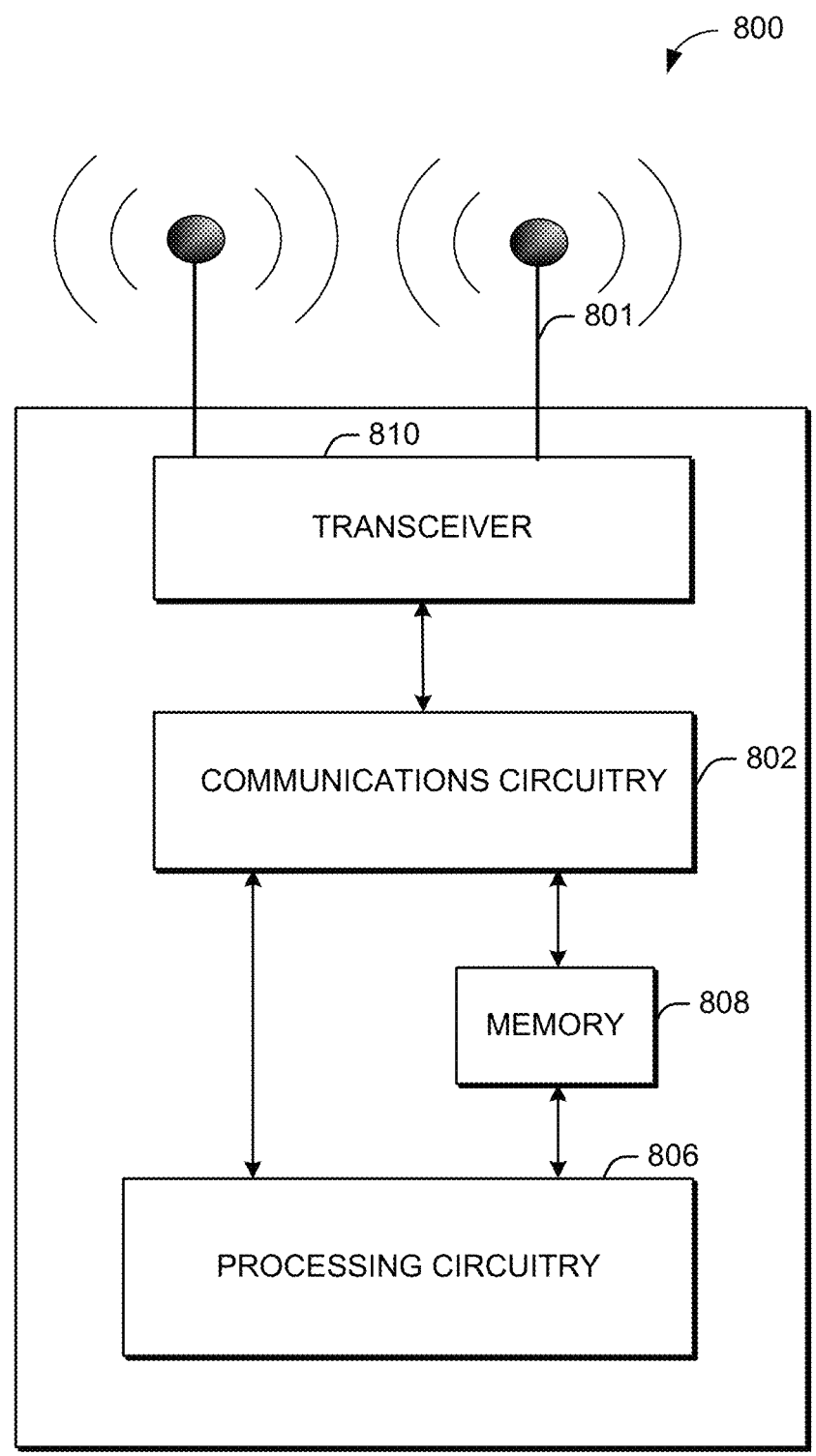
FIG. 8 is a block diagram of an example device capable of sending and receiving wireless signals, in accordance with one or more example embodiments of the disclosure.

FIG. 8 is a block diagram of an example device capable of sending and receiving wireless signals, in accordance with one or more embodiments of the disclosure. The communication station 800 may include communications circuitry 802 and a transceiver 810 for transmitting and receiving signals to and from other communication stations using one or more antennas 801. The communications circuitry 802 may include circuitry that can operate the physical layer communications and/or medium access control (MAC) communications for controlling access to the wireless medium, and/or any other communications layers for transmitting and receiving signals. The communication station 800 may also include processing circuitry 806 and memory 808 arranged to perform the operations described herein. In some embodiments, the communications circuitry 802 and the processing circuitry 806 may be configured to perform operations detailed in FIGS. 1-6.

In accordance with some embodiments, the communications circuitry 802 may be arranged to contend for a wireless medium and configure frames or packets for communicating over the wireless medium. The communications circuitry 802 may be arranged to transmit and receive signals. The communications circuitry 802 may also include circuitry for modulation/demodulation, upconversion/downconversion, filtering, amplification, etc. In some embodiments, the processing circuitry 806 of the communication station 800 may include one or more processors. In other embodiments, two or more antennas 801 may be coupled to the communications circuitry 802 arranged for sending and receiving signals. The memory 808 may store information for configuring the processing circuitry 806 to perform operations for configuring and transmitting message frames and performing the various operations described herein. The memory 808 may include any type of memory, including non-transitory memory, for storing information in a form readable by a machine (e.g., a computer). For example, the memory 808 may include a computer-readable storage device, read-only memory (ROM), random-access memory (RAM), magnetic disk storage media, optical storage media, flash-memory devices and other storage devices and media.

In some embodiments, the communication station 800 may be part of a portable wireless communication device, such as a personal digital assistant (PDA), a laptop or portable computer with wireless communication capability, a web tablet, a wireless telephone, a smartphone, a wireless headset, a pager, an instant messaging device, a digital camera, an access point, a television, a medical device (e.g., a heart rate monitor, a blood pressure monitor, etc.), a wearable computer device, or another device that may receive and/or transmit information wirelessly.

In some embodiments, the communication station 800 may include one or more antennas 801. The antennas 801 may include one or more directional or omnidirectional antennas, including, for example, dipole antennas, monopole antennas, patch antennas, loop antennas, microstrip antennas, or other types of antennas suitable for transmission of RF signals. In some embodiments, instead of two or more antennas, a single antenna with multiple apertures may be used. In these embodiments, each aperture may be considered a separate antenna. In some multiple-input multiple-output (MIMO) embodiments, the antennas may be effectively separated for spatial diversity and the different channel characteristics that may result between each of the antennas and the antennas of a transmitting station.

In some embodiments, the communication station 800 may include one or more of a keyboard, a display, a non-volatile memory port, multiple antennas, a graphics processor, an application processor, speakers, and other mobile device elements. The display may be an LCD screen including a touch screen.

Although the communication station 800 is illustrated as having several separate functional elements, two or more of the functional elements may be combined and may be implemented by combinations of software-configured elements, such as processing elements including digital signal processors (DSPs), and/or other hardware elements. For example, some elements may include one or more microprocessors, DSPs, field-programmable gate arrays (FPGAs), application specific integrated circuits (ASICs), radio-frequency integrated circuits (RFICs) and combinations of various hardware and logic circuitry for performing at least the functions described herein. In some embodiments, the functional elements of the communication station 600 may refer to one or more processes operating on one or more processing elements.

Certain embodiments may be implemented in one or a combination of hardware, firmware, and software. Other embodiments may also be implemented as instructions stored on a computer-readable storage device, which may be read and executed by at least one processor to perform the operations described herein. A computer-readable storage device may include any non-transitory memory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media. In some embodiments, the communication station 800 may include one or more processors and may be configured with instructions stored on a computer-readable storage device memory.

In some embodiments, the communication station 800 may operate as a standalone device or may be connected (e.g., networked) to other machines. In a networked deployment, the communication station 800 may operate in the capacity of a server machine, a client machine, or both in server-client network environments. In an example, the communication station 800 may act as a peer machine in peer-to-peer (P2P) (or other distributed) network environments. The communication station 800 may be a personal computer (PC), a tablet PC, a set-top box (STB), a personal digital assistant (PDA), a mobile telephone, wearable computer device, a web appliance, a network router, switch or bridge, or any machine capable of executing instructions (sequential or otherwise) that specify actions to be taken by that machine, such as a base station. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), or other computer cluster configurations.

Examples, as described herein, may include or may operate on logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer readable medium containing instructions where the instructions configure the execution units to carry out a specific operation when in operation. The configuring may occur under the direction of the executions units or a loading mechanism. Accordingly, the execution units are communicatively coupled to the computer-readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

Figure 9:
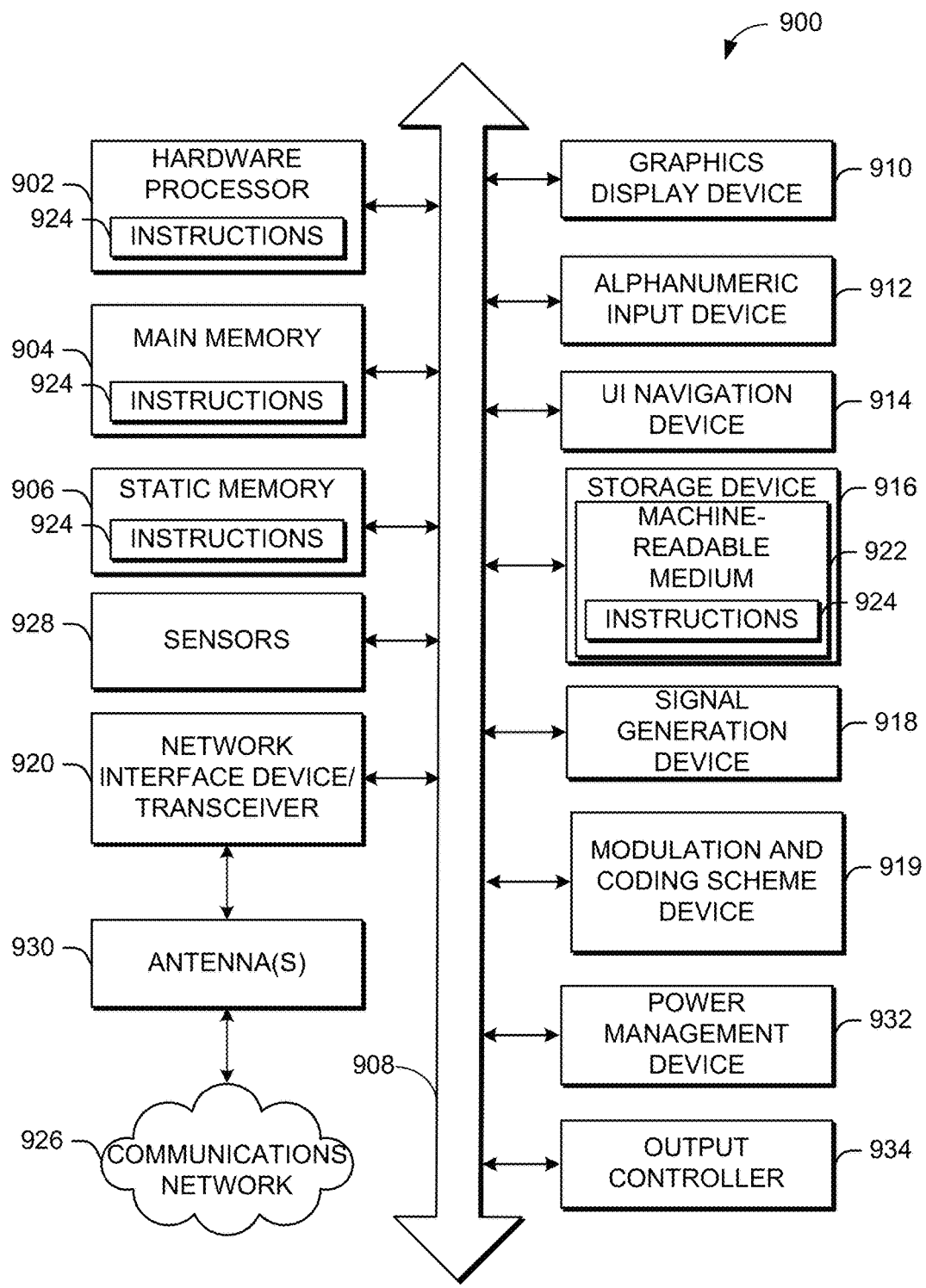
FIG. 9 is a block diagram of an example device upon which any of one or more techniques (e.g., methods) may be performed, in accordance with one or more embodiments of the disclosure.

FIG. 9 is a block diagram of an example device upon which any of one or more techniques (e.g., methods) may be performed, in accordance with one or more embodiments of the disclosure. The machine (e.g., communication system) 900 may include a hardware processor 902 (e.g., a central processing unit (CPU), a graphics processing unit (GPU), a hardware processor core, or any combination thereof), a main memory 904 and a static memory 906, some or all of which may communicate with each other via an interlink (e.g., bus) 908. The machine 900 may further include a power management device 932, a graphics display device 910, an alphanumeric input device 912 (e.g., a keyboard), and a user interface (UI) navigation device 914 (e.g., a mouse). In an example, the graphics display device 910, alphanumeric input device 912, and UI navigation device 914 may be a touch screen display. The machine 900 may additionally include a storage device (i.e., drive unit) 916, a signal generation device 918 (e.g., a speaker), an MCS codes device 919, a network interface device/transceiver 920 coupled to antenna(s) 930, and one or more sensors 928, such as a global positioning system (GPS) sensor, compass, accelerometer, or other sensor. The machine 900 may include an output controller 934, such as a serial (e.g., universal serial bus (USB), parallel, or other wired or wireless (e.g., infrared (IR), near field communication (NFC), etc.) connection to communicate with or control one or more peripheral devices (e.g., a printer, card reader, etc.)).

The storage device 916 may include a machine readable medium 922 on which is stored one or more sets of data structures or instructions 924 (e.g., software) embodying or utilized by any one or more of the techniques or functions described herein. The instructions 924 may also reside, completely or at least partially, within the main memory 904, within the static memory 906, or within the hardware processor 902 during execution thereof by the machine 900. In an example, one or any combination of the hardware processor 902, the main memory 904, the static memory 906, or the storage device 916 may constitute machine-readable media.

The MCS codes device 919 may modulate and demodulate one or more signals sent from and received at machine 900 in accordance with one or more Wi-Fi standards and/or Bluetooth standards.

While the machine-readable medium 922 is illustrated as a single medium, the term "machine-readable medium" may include a single medium or multiple media (e.g., a centralized or distributed database, and/or associated caches and servers) configured to store the one or more instructions 924.

Various embodiments may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "machine-readable medium" may include any medium that is capable of storing, encoding, or carrying instructions for execution by the machine 900 and that cause the machine 900 to perform any one or more of the techniques of the present disclosure, or that is capable of storing, encoding, or carrying data structures used by or associated with such instructions. Non-limiting machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., Electrically Programmable Read-Only Memory (EPROM), or Electrically Erasable Programmable Read-Only Memory (EEPROM)) and flash memory devices; magnetic disks, such as internal hard disks and removable disks; magneto-optical disks; and CD-ROM and DVD-ROM disks. Data 105 may be a machine readable medium.

The instructions 924 may further be transmitted or received over a communications network 926 using a transmission medium via the network interface device/transceiver 920 utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), Plain Old Telephone (POTS) networks, wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, and peer-to-peer (P2P) networks, among others. In an example, the network interface device/transceiver 920 may include one or more physical jacks (e.g., Ethernet, coaxial, or phone jacks) or one or more antennas to connect to the communications network 926. In an example, the network interface device/transceiver 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 900 and includes digital or analog communications signals or other intangible media to facilitate communication of such software. The operations and processes (e.g., process 600) described and shown above may be carried out or performed in any suitable order as desired in various implementations. Additionally, in certain implementations, at least a portion of the operations may be carried out in parallel. Furthermore, in certain implementations, less than or more than the operations described may be performed.

The word "exemplary" is used herein to mean "serving as an example, instance, or illustration." Any embodiment described herein as "exemplary" is not necessarily to be construed as preferred or advantageous over other embodiments. The terms "computing device", "user device", "communication station", "station", "handheld device", "mobile device", "wireless device" and "user equipment" (UE) as used herein refers to a wireless communication device such as a cellular telephone, smartphone, tablet, netbook, wireless terminal, laptop computer, a femtocell, High Data Rate (HDR) subscriber station, access point, printer, (PC, Desktop, PDAs, etc.), access terminal, or other personal communication system (PCS) device. The device may be either mobile or stationary.

As used within this document, the term "communicate" is intended to include transmitting, or receiving, or both transmitting and receiving. This may be particularly useful in claims when describing the organization of data that is being transmitted by one device and received by another, but only the functionality of one of those devices is required to infringe the claim. Similarly, the bidirectional exchange of data between two devices (both devices transmit and receive during the exchange) may be described as 'communicating', when only the functionality of one of those devices is being claimed. The term "communicating" as used herein with respect to a wireless communication signal includes transmitting the wireless communication signal and/or receiving the wireless communication signal. For example, a wireless communication unit, which is capable of communicating a wireless communication signal, may include a wireless transmitter to transmit the wireless communication signal to at least one other wireless communication unit, and/or a wireless communication receiver to receive the wireless communication signal from at least one other wireless communication unit.

Some embodiments may be used in conjunction with various devices and systems, for example, a Personal Computer (PC), a desktop computer, a mobile computer, a laptop computer, a notebook computer, a tablet computer, a server computer, a handheld computer, a handheld device, a Personal Digital Assistant (PDA) device, a handheld PDA device, an on-board device, an off-board device, a hybrid device, a vehicular device, a non-vehicular device, a mobile or portable device, a consumer device, a non-mobile or non-portable device, a wireless communication station, a wireless communication device, a wireless Access Point (AP), a wired or wireless router, a wired or wireless modem, a video device, an audio device, an audio-video (A/V) device, a wired or wireless network, a wireless area network, a Wireless Video Area Network (WVAN), a Local Area Network (LAN), a Wireless LAN (WLAN), a Personal Area Network (PAN), a Wireless PAN (WPAN), and the like.

Some embodiments may be used in conjunction with one way and/or two-way radio communication systems, cellular radio-telephone communication systems, a mobile phone, a cellular telephone, a wireless telephone, a Personal Communication Systems (PCS) device, a PDA device which incorporates a wireless communication device, a mobile or portable Global Positioning System (GPS) device, a device which incorporates a GPS receiver or transceiver or chip, a device which incorporates a Radio Frequency Identification (RFID) element or chip, a Multiple Input Multiple Output (MIMO) transceiver or device, a Single Input Multiple Output (SIMO) transceiver or device, a Multiple Input Single Output (MISO) transceiver or device, a device having one or more internal antennas and/or external antennas, Digital Video Broadcast (DVB) devices or systems, multi-standard radio devices or systems, a wired or wireless handheld device, e.g., a Smartphone, a Wireless Application Protocol (WAP) device, or the like.

Some embodiments may be used in conjunction with one or more types of wireless communication signals and/or systems following one or more wireless communication protocols, for example, Radio Frequency (RF), Infra Red (IR), Frequency-Division Multiplexing (FDM), Orthogonal FDM (OFDM), Time-Division Multiplexing (TDM), Time-Division Multiple Access (TDMA), Extended TDMA (E-TDMA), General Packet Radio Service (GPRS), extended GPRS, Code-Division Multiple Access (CDMA), Wideband CDMA (WCDMA), CDMA 2000, single-carrier CDMA, multi-carrier CDMA, Multi-Carrier Modulation (MDM), Discrete Multi-Tone (DMT), Bluetooth→, Global Positioning System (GPS), Wi-Fi, Wi-Max, ZigBee™, Ultra-Wideband (UWB), Global System for Mobile communication (GSM), 2G, 2.5G, 3G, 3.5G, 4G, Fifth Generation (5G) mobile networks, 3GPP, Long Term Evolution (LTE), LTE advanced, Enhanced Data rates for GSM Evolution (EDGE), or the like. Other embodiments may be used in various other devices, systems, and/or networks.

What is claimed is:

1. A system for determining the presence of a chemical substance in an environment, the system comprising:
　at least one sensor configured to:
　　detect one or more chemical substances in the environment, wherein the one or more chemical substances are illicit drugs and/or their metabolites,
　　conduct one or more electrochemical tests, wherein:
　　　each of the one or more electrochemical tests are performed on each of one or more chemical samples in the environment, by applying current to the one or more samples and measuring an electric potential of the one or more samples, and
　　generate one or more electrical signals corresponding to the one or more chemical samples in the environment;
　at least one computing device, with at least one processor, configured to:
　　receive and process the one or more electrical signals corresponding to the one or more samples from the environment, wherein at least one mobile device compares the electrical signals to:
　　　electrical signals corresponding to stored profiles of known chemical substances in the environment to determine if a match exists;
　　　electrical signals corresponding to baseline threshold values of known chemical substances expected in the environment to determine if there is an excess or lack of one or more of the known chemical substance; or
　　　the electrical signals corresponding to both the stored profiles and baseline threshold values of the one or more of the known chemical substances in the environment;
　　display an alert on the at least one mobile device to confirm or deny the presence of the chemical substance; and
　an ampoule, containing a liquid that is coupled to a swab that may be used to collect samples from the environment, wherein:
　　the liquid may be an electrolyte that is dispersed on the swab after a portion or the entire ampoule is broken, the swab may be used to collect the samples from the environment, and a plurality of electrodes may be configured to generate the electrical signals corresponding to the one or more samples from the environment.

2. The system of claim 1, wherein the at least one mobile device receives the electrical signals corresponding to the one or more chemical samples from the at least one sensor using at least one connection established between the at least one computational device and at least one sensor, wherein the at least one connection is a hardwired or wireless connection.

3. The system of claim 2, wherein the at least one sensor performs the one or more electrochemical tests by applying an anodic stripping voltammetry technique to the metallic chemical substance.

4. The system of claim 1, wherein the electrodes are screen printed electrodes.

5. The system of claim 4, wherein the electrodes comprises gold.

6. The system of claim 4, wherein the screen printed electrode comprise a testing substrate.

7. The system of claim 4, wherein the screen printed electrodes have a metallic plating.

8. The system of claim 1, comprising two or more electrodes.

9. The system of claim 1, wherein the electrolyte is a buffer solution.

10. A mobile device storing computer-readable instructions which, when executed by a processor, causes the processor to perform the operations comprising:
　detecting and storing an electrical signal, from at least one sensor corresponding to one or more chemical samples of an environment, in at least one memory, wherein the one or more chemical samples comprises one or more chemical substances that are illicit drugs and/or their metabolites;
　retrieving a stored electrical signal, from the at least one memory corresponding to one or more chemical substances in the environment;

comparing the electrical signal to known responses corresponding to predetermined chemical substances in the environment using at least one comparative analysis technique;

determining if the chemical sample from the environment corresponds to one or more of the predetermined chemical substances based at least in part on the comparison of the electrical signal to the known responses; and displaying on a display, one or more icons or text confirming or denying the presence of the chemical substances in the environment.

11. The mobile device of claim 10, wherein the at least one comparative analysis technique is an absolute maximum or minimum technique.

12. The mobile device of claim 11, wherein:

the mobile device further comprises a GPS receiver configured to store the location of the one or more chemical samples collected from the environment, and the computer-executable instructions further causes the processor to perform the operations comprising:

determining that the one or more chemical substances in a location are native to the location; and displaying an alert, on the display, confirming a chemical substance or set of chemical substances are native to the environment, or displaying a different alert, on the display, either denying or requiring further analysis to confirm or deny a chemical substance or set of chemical substances are native to the environment.

13. The mobile device of claim 12, wherein the processor preforms the comparative analysis technique on a subset of the one or more chemical samples in the environment.

14. The mobile device of claim 13, wherein the subset of the one or more chemical samples in the environment corresponds to a forensic comparative analysis technique in which the electrical signals produced by the chemical samples in the environment are associated with the illicit drugs and the corresponding metabolite.

15. The mobile device of claim 10, wherein the at least one comparative analysis technique is slope comparison technique, derivative technique, or an integration technique.

16. The mobile device of claim 10, wherein the at least one comparative analysis technique is a derivative technique.

17. The mobile device of claim 16, wherein the derivative technique comprises determining a first order derivative of the subset of the one or more chemical samples.

18. The mobile device of claim 16, wherein the derivative technique comprises determining a second order derivative of the subset of the one or more chemical samples.

19. The mobile device of claim 10, wherein the at least one comparative analysis technique is an integration technique.

* * * * *